United States Patent
Jiang et al.

(10) Patent No.: US 9,554,861 B2
(45) Date of Patent: Jan. 31, 2017

(54) MEDICAL INSTRUMENT HOLDING APPARATUS

(71) Applicant: Hiwin Technologies Corp., Taichung (TW)

(72) Inventors: Zong Sian Jiang, Taichung (TW); Wuteng Hsieh, Taichung (TW); Yan Yu Chen, Taichung (TW)

(73) Assignee: Hiwin Technologies Corp., Situn, Taichung (TW)

( * ) Notice: Subject to any disclaimer, the term of this patent is extended or adjusted under 35 U.S.C. 154(b) by 178 days.

(21) Appl. No.: 14/183,718

(22) Filed: Feb. 19, 2014

(65) Prior Publication Data

US 2015/0230870 A1   Aug. 20, 2015

(51) Int. Cl.
| | | |
|---|---|---|
| *B25J 18/02* | (2006.01) | |
| *A61B 19/00* | (2006.01) | |
| *A61B 1/00* | (2006.01) | |
| *B25J 15/04* | (2006.01) | |

(52) U.S. Cl.
CPC ............... *A61B 19/26* (2013.01); *A61B 90/50* (2016.02); *B25J 18/025* (2013.01); *A61B 1/00147* (2013.01); *B25J 15/045* (2013.01); *Y10S 901/28* (2013.01); *Y10S 901/30* (2013.01); *Y10T 74/20329* (2015.01)

(58) Field of Classification Search
CPC ..... A61B 1/00147; A61B 90/50; B25J 15/045
USPC .................................. 901/27, 29; 74/490.01
See application file for complete search history.

(56) References Cited

U.S. PATENT DOCUMENTS

| | | | | |
|---|---|---|---|---|
| 3,736,010 | A * | 5/1973 | Larkin | B64C 27/54 16/429 |
| 4,421,456 | A * | 12/1983 | Huffman | F04D 29/126 415/170.1 |
| 5,387,239 | A * | 2/1995 | Bianco | A61F 2/30 403/118 |
| 5,697,939 | A | 12/1997 | Kubota et al. | |
| 7,497,874 | B1 * | 3/2009 | Metzger | A61F 2/30721 623/20.15 |
| 2006/0037797 | A1 * | 2/2006 | Mathon | B62K 21/00 180/219 |
| 2011/0271786 | A1 * | 11/2011 | Long | B25J 9/108 74/490.05 |

* cited by examiner

*Primary Examiner* — William C Joyce
*Assistant Examiner* — Randell J Krug
(74) *Attorney, Agent, or Firm* — Charles E. Baxley

(57) ABSTRACT

A medical instrument holding apparatus includes a shaft slidably engaged into a housing and movable into and out of the housing, the housing includes a guiding member engaged with the shaft for guiding and limiting the shaft to slide relative to the housing only and for preventing the shaft from being rotated relative to the housing, a locking device is engaged onto the shaft and includes a positioning member for engaging with an anchoring member of the shaft and for locking the shaft and the housing together, and one or more fasteners are engaged with the housing and the locking device for securing the shaft and the housing together with the locking device.

2 Claims, 7 Drawing Sheets

MEDICAL INSTRUMENT HOLDING APPARATUS

BACKGROUND OF THE INVENTION

1. Field of the Invention

The present invention relates to a medical instrument holding or supporting apparatus, and more particularly to a medical instrument holding or supporting apparatus including an improved or simplified structure or configuration that may be easily and quickly made or manufactured by the manufacturers and that may be adjusted to different length for conducting different medical surgery or medical operation.

2. Description of the Prior Art

Typical medical instruments, such as rigidoscopes, laparoscopes, endoscopes, trocars, treating instruments, or the other medical instruments or the like have been developed and widely provided and used for conducting or operating an operation on a patient, and are typically grasped and held by the hands of the operators, such as the doctors, and it will be difficult for the operators or the doctors to hold the medical instruments and to conduct or operate the operation on the patient.

Normally, the medical instruments are grasped and held by one of the operators or the doctors, and the other operator or doctor will stand beside the medical instruments holding operator and will both standing near the patient at the same time, in a tiny or narrowed operation room.

For allowing the medical instruments to be held in place without being grasped by the operators or the doctors, a scope-holder has been disclosed and used to hold the medical instruments in place, for inserting the medical instruments into the abdominal cavity of a patient.

For example, U.S. Pat. No. 5,697,939 to Kubota et al. discloses one of the typical medical instrument holding apparatuses comprising a plurality of arms sections and holding sections for holding and grasping the treating instrument or medical instrument and for engaging or inserting the treating or medical instruments into the abdominal cavity of the patient.

However, the typical medical instrument holding apparatuses comprise a rather complicated structure or configuration having a number of parts or elements that may not be easily and quickly made or manufactured and that may not be easily used to conduct the operation on the patient.

The present invention has arisen to mitigate and/or obviate the afore-described disadvantages of the conventional medical instrument holding apparatuses.

SUMMARY OF THE INVENTION

The primary objective of the present invention is to provide a medical instrument holding or supporting apparatus including an improved or simplified structure or configuration that may be easily and quickly made or manufactured by the manufacturers and that may be adjusted to different length for conducting different medical surgery or medical operation.

In accordance with one aspect of the invention, there is provided a medical instrument holding apparatus comprising a housing including a chamber formed therein, a shaft slidably engaged into the chamber of the housing and movable into and out of the chamber of the housing, the shaft including an anchoring member provided thereon, the housing including a guiding member extended into the chamber of the housing and engaged with the shaft for guiding and limiting the shaft to slide relative to the housing only and for preventing the shaft from being rotated relative to the housing, a locking device including a bore formed therein for slidably receiving and engaging with the shaft, and the locking device including a positioning member for selectively engaging with the anchoring member of the shaft and for locking the shaft and the housing together, and at least one fastener engaged with the housing and the locking device for locking the locking device to the housing and for securing the shaft and the housing together with the locking device.

The anchoring member of the shaft is selected from an outer thread. The positioning member the locking device is selected from an inner thread for selectively engaging with the outer thread of the shaft. A gripping mechanism may further be provided and disposed on a free end portion of the shaft.

A supporting mechanism may further be provided and includes a supporting arm having a pivot member, the housing is provided on the pivot member of the supporting arm. The supporting mechanism includes a base, and the supporting arm includes a lower portion rotatably attached on the base with a pivot device, and the pivot member is provided or attached on an upper portion of the supporting arm.

Further objectives and advantages of the present invention will become apparent from a careful reading of the detailed description provided hereinbelow, with appropriate reference to the accompanying drawings.

DETAILED DESCRIPTION OF THE PREFERRED EMBODIMENT

Figure 1:
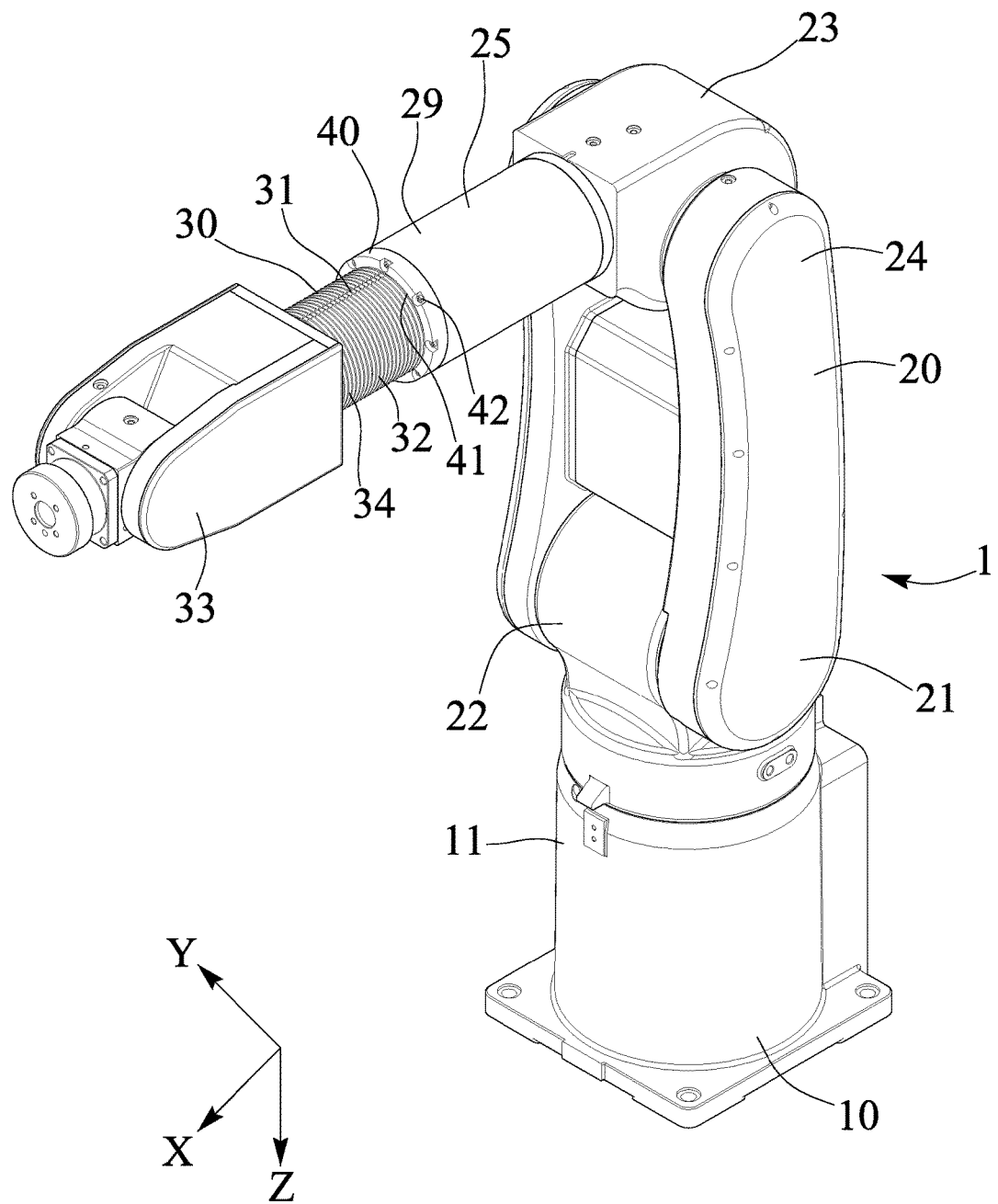
FIG. 1 is a perspective view of a medical instrument holding or supporting apparatus in accordance with the present invention.
Figure 2:
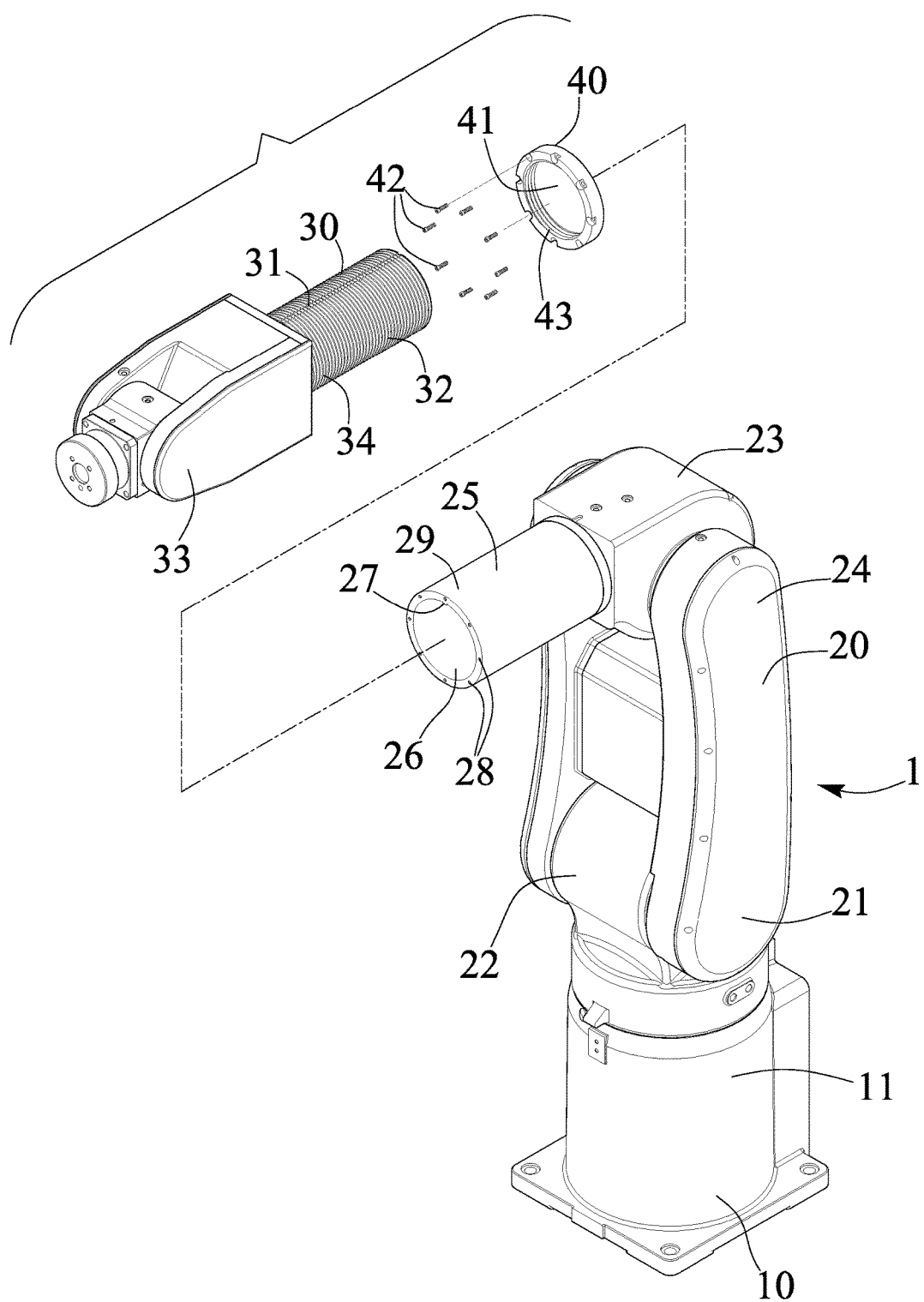
FIG. 2 is a partial exploded view of the medical instrument holding or supporting apparatus.
Figure 3:
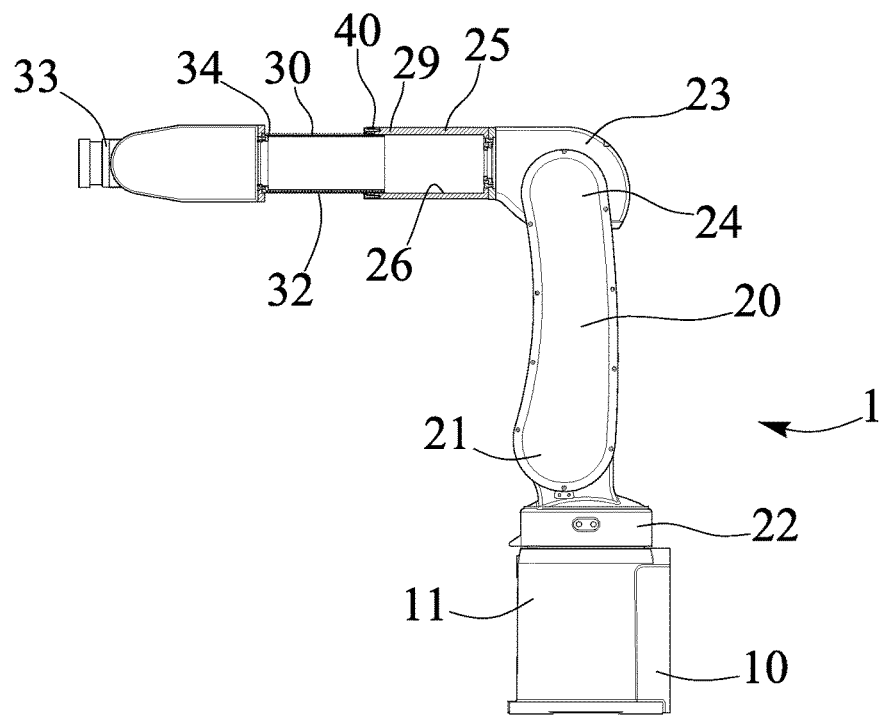
FIG. 3 is a side plan schematic view of the medical instrument holding or supporting apparatus, in which a portion of the apparatus has been cut off for showing the inner structure of the apparatus.

Referring to the drawings, and initially to FIGS. 1, 2 and 3, a medical instrument holding or supporting apparatus in accordance with the present invention comprises a supporting device or mechanism 1 including a stand or base 10 for being disposed or attached or mounted or secured on a supporting surface or ground or the like, and including a supporting arm 20 having a lower or bottom portion 21 pivotally or rotatably attached or mounted or secured on the upper portion 11 of the base 10 with a pivot joint or member or device 22 and arranged for allowing the supporting arm 20 to be pivoted or rotated relative to the base 10 freely around a Z-axis or longitudinal axis of the base 10 for 360 degrees, and arranged for allowing the supporting arm 20 to be pivoted or rotated relative to the pivot device 22.

Figure 7:
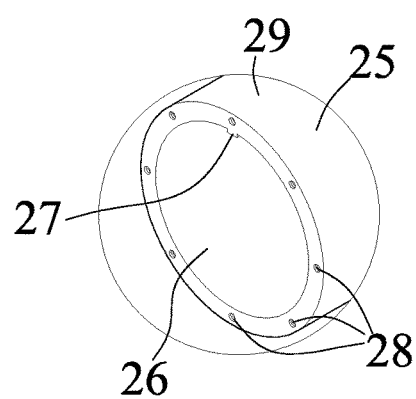
FIG. 7 is an enlarged partial perspective view illustrating a housing of the medical instrument holding or supporting apparatus.
Figure 8:
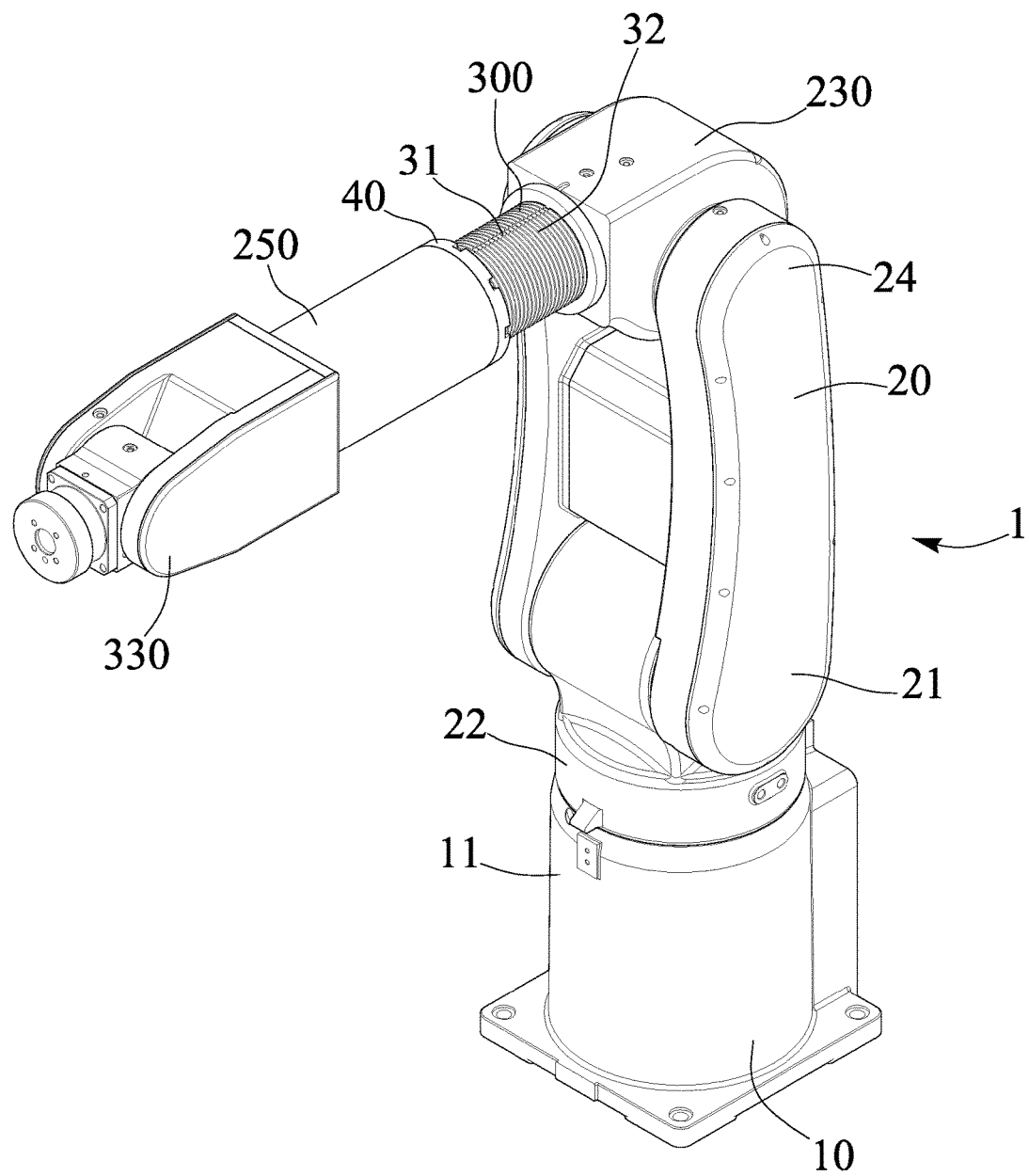
FIG. 8 is another perspective view similar to FIG. 1, illustrating the other arrangement of the medical instrument holding or supporting apparatus.
Figure 9:
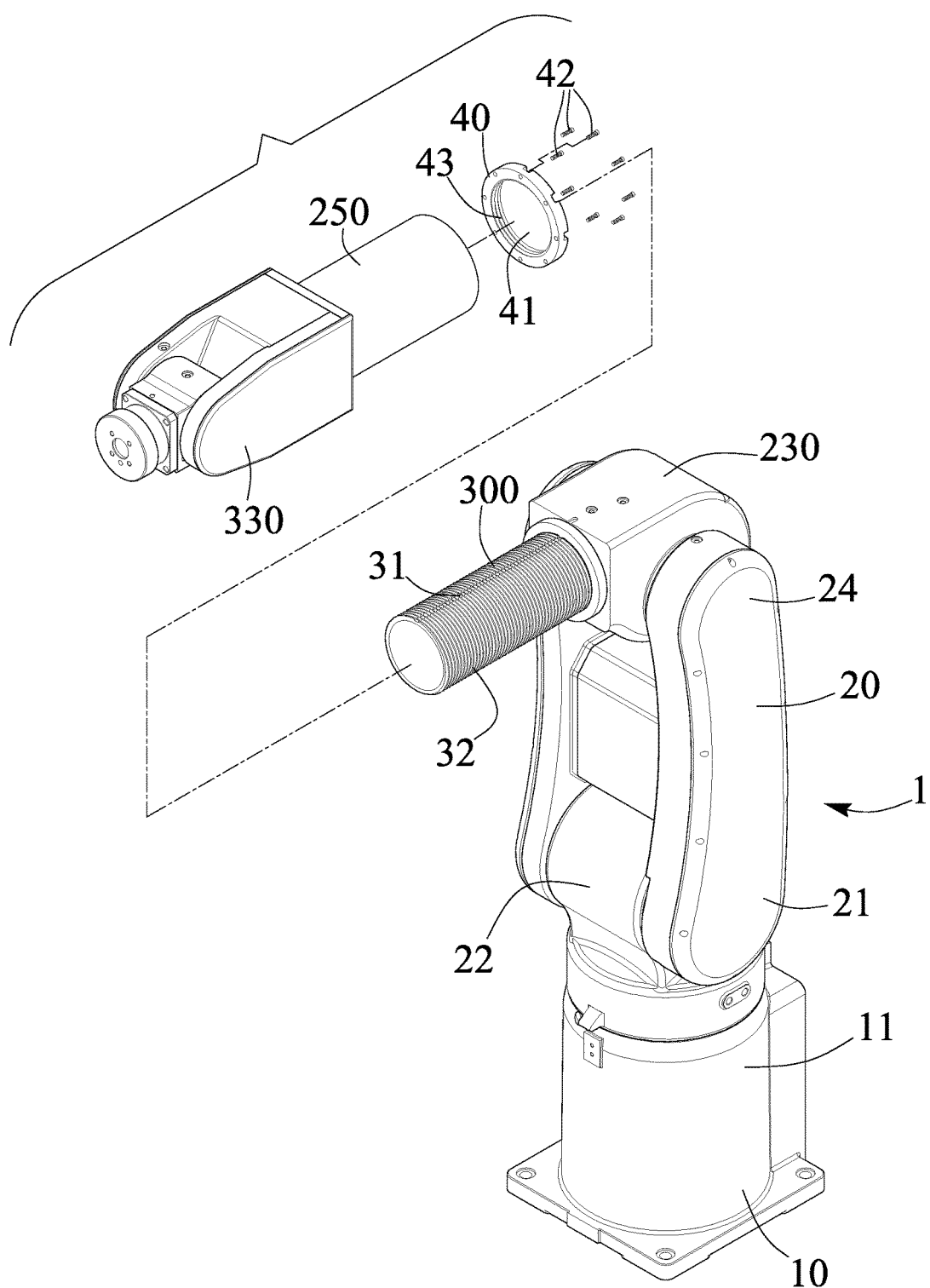
FIG. 9 is a partial exploded view of the medical instrument holding or supporting apparatus as shown in FIG. 8.
Figure 10:
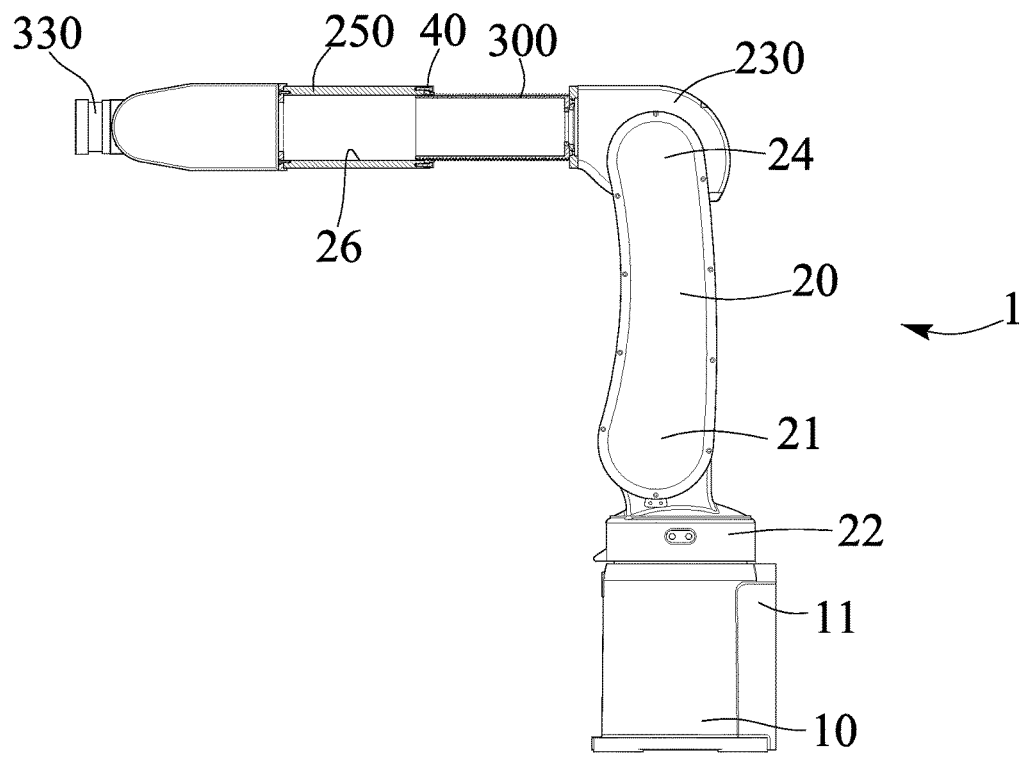
FIGS. 10, 11 are side plan schematic views illustrating the operation of the medical instrument holding or supporting apparatus as shown in FIGS. 8 and 9.
Figure 11:
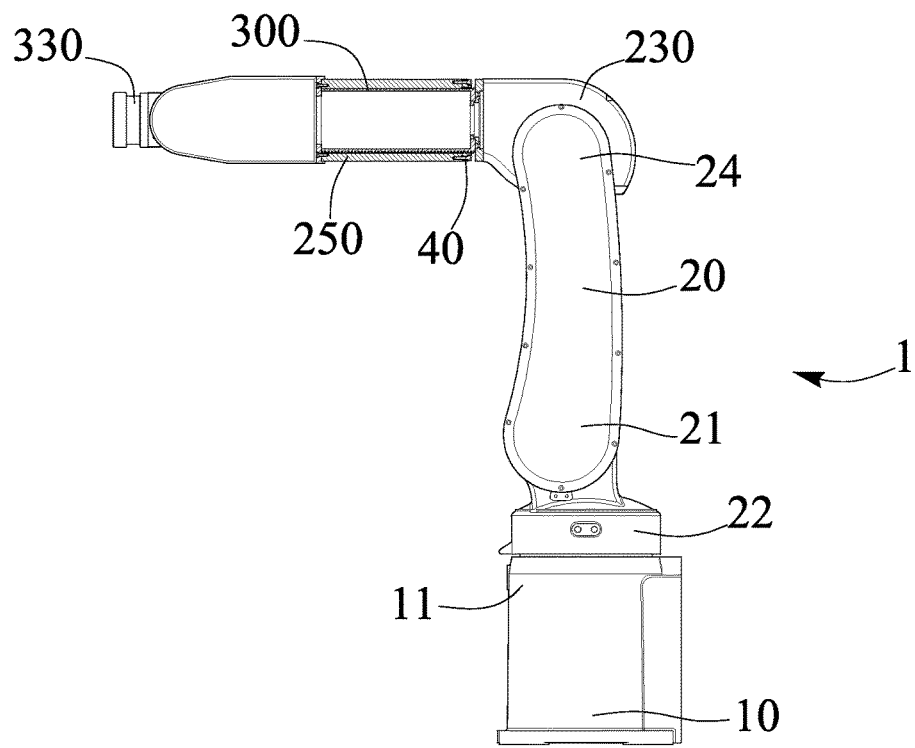

The supporting arm 20 further includes another pivot device or joint or member 23 formed or provided or disposed or engaged on the upper portion 24 of the supporting arm 20 and arranged to be pivoted or rotated relative to the supporting arm 20, the pivot member 23 includes a sleeve or cylindrical or tubular element or barrel or housing 25 provided or attached or extended forwardly therefrom and arranged or extended along the X-axis, for example. The housing 25 includes a bore or chamber 26 formed therein, and includes a longitudinal guiding flange or rib or member 27 extended into the chamber 26 of the housing 25 (FIGS. 2, 7) and parallel to the housing 25, and includes a number of orifices or screw holes 28 formed or provided in the outer or free end portion 29 thereof, and arranged equally spaced from each other.

A follower or sliding member or shaft 30 is engageable with or into the chamber 26 of the housing 25 and movable or adjustable relative to the housing 25 and movable or slidable into and out of the chamber 26 of the housing 25, and includes a longitudinal guiding groove or channel or element 31 formed in the outer peripheral portion thereof for slidably receiving or engaging with the longitudinal guiding member 27 of the housing 25 and for guiding or limiting the shaft 30 to slide or move relative to or along the housing 25 and for preventing the shaft 30 from being pivoted or rotated relative to the housing 25, and includes a positioning or retaining or anchoring member 32, such as an outer thread 32 formed or provided thereon, and includes a holding or grasping or gripping mechanism 33 formed or provided or disposed on the outer or free end portion 34 of the shaft 30 and provided for holding and grasping a treating or medical instrument (not illustrated).

For example, the treating or medical instrument may be selected from a rigidoscope, laparoscope, endoscope, trocar, treating instrument, or the other medical instruments. However, the treating or medical instrument is typical and is not related to the present invention and will not be described in further details. The treating or medical instrument holding or grasping or gripping mechanism 33 is thus formed or provided or disposed on or extended from the outer or free end portion 34 of the shaft 30 and moved in concert with the shaft 30 relative to the housing 25, and arranged for allowing the shaft 30 and the gripping mechanism 33 and thus the treating or medical instrument to be moved or adjusted toward or away from the housing 25.

The medical instrument holding or supporting apparatus in accordance with the present invention further comprises a latching or anchoring or retaining or positioning or locking ring or device 40 including a chamber or bore 41 formed therein for slidably receiving or engaging with the shaft 30 and for allowing the locking device 40 to be slidably attached or engaged onto the shaft 30, and the locking device 40 is selectively locked or secured or fastened to the housing 25 with latches or bolts or screws or fasteners 42 or the like, in which, as shown in FIGS. 1-6, the fasteners 42 are threaded or engaged with the screw holes 28 that are formed or provided in the outer or free end portion 29 of the housing 25. The locking device 40 further includes another anchoring or retaining or positioning member 43, such as an inner thread 43 formed or provided therein for selectively engaging with the outer thread 32 of the shaft 30 and for selectively latching or anchoring or retaining or locking or positioning or securing the shaft 30 and the housing 25 together with the locking device 40.

Figure 4:
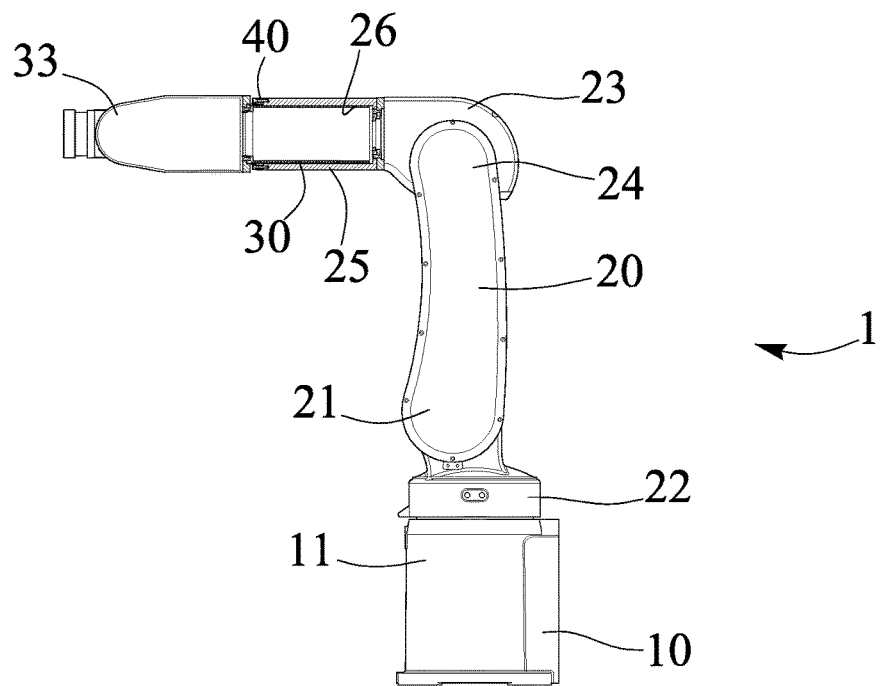
FIG. 4 is another side plan schematic view similar to FIG. 3, illustrating the operation of the medical instrument holding or supporting apparatus.
Figure 5:
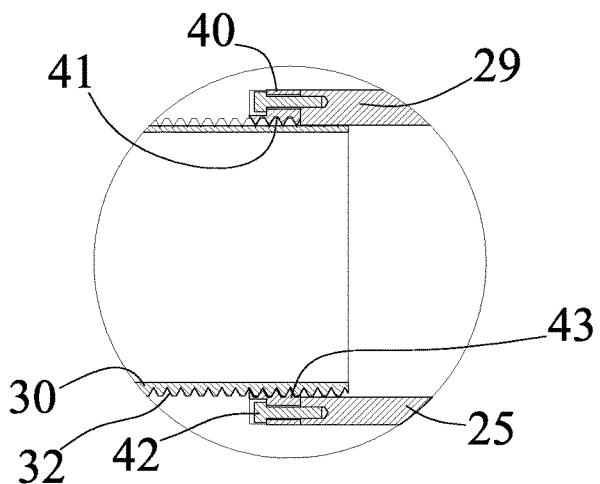
FIGS. 5, 6 are enlarged partial cross sectional views of the medical instrument holding or supporting apparatus as shown in FIGS. 3 and 4 respectively.
Figure 6:
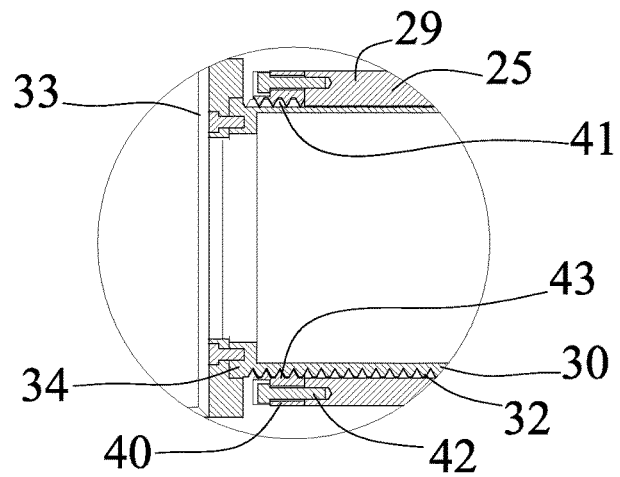

In operation, the longitudinal guiding member 27 of the housing 25 is slidably received or engaged in the longitudinal guiding channel or element 31 of the shaft 30 for guiding or limiting the shaft 30 only to slide or move relative to or along the housing 25 and for preventing the shaft 30 from being pivoted or rotated relative to the housing 25, and thus for allowing the shaft 30 and the gripping mechanism 33 and thus the treating or medical instrument to be moved or adjusted toward or away from the housing 25 selectively (FIGS. 3, 4). After the housing 25 and the shaft 30 have been adjusted relative to each other to the required location or position, as shown in FIGS. 3-6, the locking device 40 may be moved or rotated or adjusted relative to the shaft 30 and may be locked or secured or fastened to the housing 25 with the fasteners 42 or the like for preventing the shaft 30 from being pivoted or rotated and moved relative to the housing 25.

It is to be noted that the adjustable or sliding engagement or attachment mechanism or structure or configuration of the shaft 30 relative to the housing 25 allows the gripping mechanism 33 and thus the treating or medical instrument to be supported at different location or position for conducting different medical surgery or medical operation. Alternatively, as shown in FIGS. 8-11, the shaft 300 may be provided or attached or extended forwardly from the pivot member 230 of the supporting arm 20, and the housing 250 may include the holding or grasping or gripping mechanism 330 formed or provided or disposed thereon for holding and grasping the treating or medical instrument (not illustrated) and may be movably or adjustably or slidably attached or engaged onto the shaft 300, and may be locked or secured or fastened to the shaft 300 with the locking device 40.

Accordingly, the medical instrument holding apparatus in accordance with the present invention includes an improved or simplified structure or configuration that may be easily and quickly made or manufactured by the manufacturers and that may be adjusted to different length for conducting different medical surgery or medical operation.

Although this invention has been described with a certain degree of particularity, it is to be understood that the present disclosure has been made by way of example only and that numerous changes in the detailed construction and the combination and arrangement of parts may be resorted to without departing from the spirit and scope of the invention as hereinafter claimed.

We claim:

1. A holding apparatus comprising:
    a supporting mechanism including a base, and including a supporting arm, said supporting arm including a lower portion rotatably attached on said base with a pivot device, said supporting mechanism including a pivot member provided on an upper portion of said supporting arm,
    a housing provided on said pivot member of said supporting arm, and including a chamber formed in said housing, said housing including an outer free end portion, and including a plurality of screw holes formed in the outer free end portion of the housing,
    a shaft slidably engaged into said chamber of said housing and movable into and out of said chamber of said housing, said shaft including an anchoring member provided thereon, said anchoring member of said shaft being selected from an outer thread, and said shaft including a longitudinal guiding element formed in an outer peripheral portion thereof, a gripping mechanism disposed on a free end portion of said shaft, said housing including a guiding member extended into said chamber of said housing and slidably engaged with said longitudinal guiding element of said shaft for guiding and limiting said shaft to slide relative to said housing only and for preventing said shaft from being rotated relative to said housing, a locking device including a bore formed therein for slidably receiving and engaging with said shaft, and said locking device including a positioning member for selectively engaging with said anchoring member of said shaft and for locking said shaft and said housing together, said positioning member of said locking device being selected from an inner thread for selectively engaging with said outer thread of said shaft, and a plurality of fasteners engaged with said locking device and engaged with said screw holes that are formed in the outer free end portion of said housing for locking said locking device to said housing and for securing said shaft and said housing together with said locking device.

2. The holding apparatus according to claim 1, wherein said screw holes that are formed in the outer free end portion of said housing and arranged equally spaced from each other.

* * * * *